United States Patent
Menuhr et al.

(10) Patent No.: US 6,716,156 B2
(45) Date of Patent: Apr. 6, 2004

(54) CAPSULE SEED

(75) Inventors: Helmut Menuhr, Braunschweig (DE); Eberhard Fritz, Braunschweig (DE); Mark Shilton, Didcot (GB)

(73) Assignee: AEA Technology OSA GmbH (DE)

( * ) Notice: Subject to any disclaimer, the term of this patent is extended or adjusted under 35 U.S.C. 154(b) by 0 days.

(21) Appl. No.: 10/066,918

(22) Filed: Feb. 4, 2002

(65) Prior Publication Data

US 2002/0156338 A1 Oct. 24, 2002

(30) Foreign Application Priority Data

Feb. 15, 2001 (EP) .......................... 01103825
Mar. 20, 2001 (EP) .......................... 01106951

(51) Int. Cl.$^7$ ................................ A61N 5/00
(52) U.S. Cl. ........................................... 600/8
(58) Field of Search ................ 600/8; 376/158, 376/169, 184, 186, 202

(56) References Cited

U.S. PATENT DOCUMENTS

| | | | |
|---|---|---|---|
| 3,351,049 A | 11/1967 | Lawrence | 128/1.2 |
| 4,994,013 A | 2/1991 | Suthanthiran et al. | |
| 5,163,896 A | 11/1992 | Suthanthiran et al. | |
| 5,342,283 A | * 8/1994 | Good | 600/8 |
| 5,713,828 A | 2/1998 | Coniglione | |

FOREIGN PATENT DOCUMENTS

| | | | | |
|---|---|---|---|---|
| EP | 1 008 995 A1 | 6/2000 | ............ | G21G/4/08 |
| EP | 1 060 764 A1 | 12/2000 | ............ | A61N/5/10 |
| EP | 1 060 765 A1 | 12/2000 | ............ | A61N/5/10 |
| EP | 1 084 733 A1 | 3/2001 | ............ | A61N/5/10 |
| WO | WO 86/04248 | 7/1986 | ............ | A61N/5/10 |
| WO | WO 97/19706 | 6/1997 | ............ | A61K/51/12 |
| WO | WO 99/33063 | 7/1999 | ............ | G21G/1/10 |
| WO | WO 99/39765 | 8/1999 | | |
| WO | WO 99/51299 | 10/1999 | | |
| WO | WO 00/27477 | 5/2000 | ............ | A61N/5/00 |
| WO | WO 02/065479 A1 | 8/2002 | ............ | G21G/4/08 |

* cited by examiner

*Primary Examiner*—Eric F. Winakur
*Assistant Examiner*—Nikita R Veniaminov
(74) *Attorney, Agent, or Firm*—Pendorf & Cutliff

(57) ABSTRACT

A radioactive or activatable seed for use in brachytherapy, and a method for producing the seed, the seed comprising a closed and self-supported casing consisting of (a) a radioactive or activatable metallic material selected from the group consisting of a metal, an alloy and a metal composite or mixtures thereof, optionally in combination with (b) a non-radioactive, non-activatable metallic material; wherein (a) comprises a radioactive nuclide selected from the group consisting of Pd-103, Tm-170, Sr-90, Y-90, Yb-169, P-32, Ge-71, Se-75, Cl-36, Ta-182, Tl-204, Re-188, W-188, Ce-144, Pr-144, Sn-123, Ru-106, Rh-106 and mixtures thereof, and/or an activatable precursor nuclide thereof selected from the group consisting of Pd-102, Rh-103, Tm-169, Y-89, Yb-168, P-31, Ge-70, Se-74, Cl-35, Ta-181, Tl-203, W-186, Sn-122 and mixtures thereof, excluding metallic Pd with natural abundance of Pd-102.

21 Claims, 2 Drawing Sheets

CAPSULE SEED

SUMMARY OF THE INVENTION

The present invention relates to a radioactive or activatable seed used for brachytherapy, in particular for restenosis treatment and tumour therapy. The invention further relates to a method for producing said radioactive or activatable seed.

BACKGROUND OF THE INVENTION

Radiation therapy is a well-established method for treating various types of illnesses including cancers such as prostate cancer and mamma carcinoma. Presently, such radiation therapy is typically carried out by using miniature medical radiation sources, so-called seeds, either by employing individual seeds or a multitude of seeds, e.g. a "train of seeds". Such seeds have also been used subsequent to treatment of arteriosclerosis and arthrosclerosis by balloon angioplasty in order to prevent restenosis due to the growth of scar tissue. All of these therapy forms are herein addressed as brachytherapy.

Brachytherapy targets the tissue adjacent to the radiation source while keeping the radiation effects on surrounding healthy tissue to a minimum. A major advantage of this form of treatment is therefore that it concentrates the emitted radiation at the site where the treatment is needed, while keeping the amount of radiation transmitted to the healthy tissue far below what it otherwise would be, if the radiation were beamed into the body from an external source using teletherapy.

Radiation brachytherapy is normally practiced in one of three ways: (1) By placing the source or sources within the tissue to be treated, i.e. interstitial therapy (e.g. mamma carcinoma); (2) by placing the source or sources inside a body cavity normally in association with the positioning device to irradiate the tissue surrounding the cavity, i.e. intracavitary therapy (e.g. prostate cancer); or (3) by placing the source or sources within a vessel or duct, normally in association with a catheter, to treat the tissue surrounding the vessel or duct, i.e. intraluminal therapy (e.g. restenosis).

Typically the radiation sources for brachytherapy are either introduced or implanted for short terms and are later removed from the body or are implanted for a longer term and may even remain permanently in the patient after treatment. The implanted sources or seeds typically comprise a radionuclide absorbed on or distributed throughout a carrier which is positioned inside a non-radioactive and preferably non-activatable biocompatible casing such as a welded metal tube. For monitoring purposes the seeds may further comprise radio-opaque markers within the casing. Such radio-opaque markers comprise high Z elements and are arranged within the casing in association with or separated from the carrier of the chosen isotope.

DESCRIPTION OF THE RELATED ART

Prior art casings function as non-radioactive diffusion barriers that prevent migration of radioactive particles into the surrounding tissue. They further provide sufficient mechanical stability, biocompatibility and corrosion-resistance to the seed. Since the casing material absorbs radiation to a certain extent, the amount of radioactive material which is positioned inside the casing has to be increased to allow for the desired emission to be achieved. To minimize this effect the casing thus typically comprises a low shielding material such as Ti and/or Al.

Sources of high radiation intensity including nuclides such as Ra-226, Cs-137 or Au-198 have been and are still used. The most commonly used radionuclides for brachytherapy are, however, iodine 125 and palladium 103 due to their radiation spectrum, dosages and halflives. For example, U.S. Pat. No. 3,351,049 describes seeds with an encapsulating outer shell containing the radiation-emitting isotopes I-125 or Pd-103. In these seeds an encapsulation shell localizes the radioactivity by physically preventing the radionuclide from migrating to other parts of the body.

U.S. Pat. Nos. 4,994,013 and 5,163,896 disclose a pellet for radioactive seeds, suitable for use in certain medical radiological treatments, comprising a metallic X-ray detectable marker rod coated with a polymeric material wherein or on which the radioactive material is adsorbed. The pellets are encapsulated in a material such as titanium to form an effectively sealed radioactive seed.

WO 97/19706 discloses a radioactive composite for use in therapeutic applications such as brachytherapy consisting essentially of a polymeric material and fine radioactive particles that are dispersed within the polymeric material. Compared to metallic casings or shells polymeric materials disclosed in WO 97/19 706 have a reduced stability towards mechanical strain or activation procedures and are less resistant to body fluids. According to WO 97/19 706 the radioactive composite can even be disintegrated e.g. by biodegradation in the patient's body after a predetermined period.

WO 86/04 248 discloses Pd-103 particles or seeds that are manufactured for implantation into turnours within a human body for emitting X-rays to destroy or reduce the tumors. The seeds contain palladium which is substantially enriched in palladium-102 and which is activated by exposure to neutron flux so as to contain X-ray emitting Pd-103. The palladium is distributed in or throughout a base material. The base material is then in turn encased in an elongated shell which is non-radioactive and non-activatable.

European patent application EP-A-I,OO8,995 discloses a radioactive palladium-103 miniature radiation source (seed) wherein the carrier matrix consists of a porous and mechanically stable inorganic material, the pores of which contain Pd-103 as a metal or in the form of a stable and water-insoluble Pd-103 compound. Preferred and exemplified are ceramic matrices. Mandatory to the seed disclosed is the porous nature of the matrix which is necessary for absorbing by capillary forces the solution comprising a soluble Pd-103 compound. After absorption the soluble Pd-103 is converted to its final insoluble form. The active carrier matrix is then encapsulated in a corrosion-resistant and body-compatible material, the encapsulating material itself being non-radioactive.

In general, there are two possibilities for producing radioactive devices. The first method refers to the use of radioactive material, i.e. material being radioactive throughout at least in part of the manufacturing process. This method is commonly called "hot" assembly. In practice, additional safety measures are necessary to avoid any direct contact with or contamination by the radioactive material. This method is mandatory for naturally occurring radioactive nuclides, nuclides obtained as fission products from nuclear fission and radionuclides which cannot be obtained from inactive precursors via a later activation step such as neutron bombardment.

Alternatively an activatable material, i.e. a material which can be converted to a radioactive material, is used and activation occurs subsequent to complete assembly. This method is called "cold" assembly. Cold assembly typically requires careful choice of seed materials with respect to stability during activation and generation of radioactive impurities.

Following the above discussion most of the prior art brachytherapy devices use non-radioactive and non-activatable (in that they do not activate to produce undesirable impurities) biocompatible metallic casings resistant to mechanical strain and body fluids, typically Ti. However, since these materials absorb radioactive radiation to a certain extent i.e. exert a shielding effect to the emitted radiation, all these devices need an increased amount of radioactive or activatable material inside the casing to allow for emission of a desired therapeutically effective radiation dose and thus to produce a desired therapeutic effect. Another disadvantage is that the shielding effect strongly depends on geometry and thickness of the casing.

It is therefore an object of the present invention to overcome these drawbacks and, in particular, to provide a radiation source for radiation therapy (seed), especially for tumor therapy and restenosis treatment, with a reduced amount of radioactive material producing a sufficient therapeutic effect, which seed is also resistant to mechanical strain and body fluids.

Furthermore, it is an object of the present invention to provide a method for producing such a radiation source.

SUMMARY OF THE INVENTION

These objects are solved by the radioactive or activatable seed and the method of producing this seed.

More in detail, according to the present invention there is provided a radioactive or activatable seed comprising a closed and self-supported casing consisting of (a) a radioactive or activatable metallic material selected from the group consisting of a metal, an alloy and a metal composite or mixtures thereof, optionally in combination with (b) a non-radioactive, non-activatable metallic material; wherein (a) comprises a radioactive nuclide selected from the group consisting of Pd-103, Tm-170, Sr-90, Y-90, Yb-169, P-32, Ge-71, Se-75, Cl-36, Ta-182, Tl-204, Re-188, W-188, Ce-144, Pr-144, Sn-123, Ru-106, Rh-106 and mixtures thereof, and/or an activatable precursor nuclide thereof selected from the group consisting of Pd-102, Rh-103, Tm-169, Y-89, Yb-168, P-31, Ge-70, Se-74, Cl-35, Ta-181, Tl-203, W-186, Sn-122 and mixtures thereof, excluding metallic Pd with natural abundance of Pd-102.

According to another embodiment of the present invention there is provided a method of preparation of a radioactive or activatable seed comprising the steps of:

a) providing the body of a closed and self-supported casing consisting of (a) a radioactive or activatable metallic material selected from the group consisting of a metal, an alloy and a metal composite or mixtures thereof, optionally in combination with (b) a non-radioactive, non-activatable metallic material; wherein (a) comprises a radioactive nuclide selected from the group consisting of Pd-103, Tm-170 Sr-90 Y-90 Yb-169 P-32 Ge-71 Se-75 Cl-36 Ta-182 Tl-204 Re-188, W-188, Ce-144, Pr-144, Sn-123, Ru-106, Rh-106 and mixtures thereof, and/or an activatable precursor nuclide thereof selected from the group consisting of Pd-102, Rh-103, Tm-169, Y-89, Yb-168, P-31, Ge-70, Se-74, Cl-35, Ta-181, Tl-203, W-186, Sn-122 and mixtures thereof, excluding metallic Pd with natural abundance of Pd-102;

b) optionally inserting a radio-opaque marker and/or a filler;

c) closing the casing; and d) optionally providing one or more coating(s).

BRIEF DESCRIPTION OF THE FIGURES

In the following the invention will be described in greater detail by reference to the illustrative embodiments shown in the figures. There are shown

DETAILED DESCRIPTION OF THE INVENTION

Figure 1:
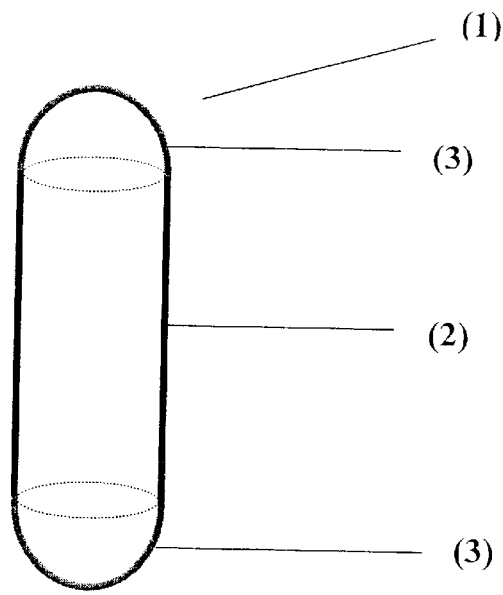
FIG. 1 shows a closed and self-supported casing (1) of the invention.

As described above the present invention in general provides a radioactive or activatable seed comprising a closed and self-supported casing or capsule consisting of (a) a metallic material comprising a radioactive nuclide and/or an activatable precursor nuclide thereof, and optionally (b) a non-radioactive, non-activatable metallic material.

It is intended that the term "self-supported casing" as used herein encompasses any hollow body which does not need a support to maintain its structure. Coatings do not represent self-supported casings in accordance with the present invention, since they are inseparably linked with a support of a specific shape. The term "casing" is further intended to refer to any closed, preferably sealingly closed three dimensional structure having an internal cavity or enclosed volume. The shape of the casing generally is not limited, except for practical reasons. Preferably, the casing is of tubular or cylindrical shape as discussed below.

The metallic material(s) (a) optionally together with (b) form(s) a non-porous body of the casing which definition may encompass parts, e.g. closures or sealing members of or for the casing being made from a differing or the same material (e.g. end caps welded to a tube and made from the same or different metallic material as the tube). Preferred embodiments will be illustrated below.

The term "metallic" as used herein refers to a material having metallic processing properties and forms a non-porous surface. This does not require the entire casing to be metallic as long as the above requirement is met. The casing may thus comprise compounds such as salts, oxides, carbides, nitrides or carbonitrides. Any non-metallic components are, however, only present to such an extent that the metallic processing properties are still preserved. Due to its consisting of the metallic material, the casing of the invention is mechanically stable (i.e. forms a capsule) and can be processed by known metallurgic methods, particularly by welding.

The casing, i.e. the metallic material and/or a coating provided thereon, preferably is chemically inert and resistant to body fluids (especially corrosion resistant), even in the case of long-term applications. Storage of these casings over an extended period of time does not substantially alter these properties. Prior art seeds comprising polymeric materials can in contrast show degradation when exposed to light or oxygen. In addition, due to the metallic material making up the casing of the invention this casing is not brittle when subjected to mechanical strain or loads in contrast to e.g., rigid polymeric or ceramic supports.

As defined above, the casing of the invention consists of (a) a radioactive or activatable metallic material selected from metals, an alloy, a metal composite or mixtures thereof, optionally in combination with (b) a non-radioactive, non-activatable metallic material. The metallic material (a) comprises a radioactive nuclide selected from the group consisting of Pd-103, Tm-170, Sr-90, Y-90, Yb-169, P-32, Ge-71, Se-75, Cl-36, Ta-182, Tl-204, Re-188, W-188, Ce-144, Pr-144, Sn-123, Ru-106, Rh-106 and mixtures thereof, and/or an actavatable precursor nuclide thereof selected from the group consisting of Pd-102, Rh-103, Tm-169, Y-89, Yb-168, P-31, Ge-70, Se-74, Cl-35, Ta-181, Tl-203, W-186, Sn-123 and mixtures thereof, excluding metallic Pd with natural abundance of Pd-102. Preferably the radioactive nuclide is one of Tm-170, Pd-103 and Sr-90. Preferably the precursor nuclide is Tm-169 or Pd-102.

The terms "radioactive nuclide" or "nuclide" are used interchangeably herein and refer to any of the above radiation emitting nuclides. The terms "activatable precursor nuclide" and "precursor nuclide" are used interchangeably herein and refer to any isotope of an element which can be converted by an activation treatment to the desired nuclide. Typically most of the nuclides and the precursor nuclides chemically are isotopes of the same element, differing in number of nuclear neutrons and thus differing in molecular weight. According to another embodiment, the radioactive nuclide may also comprise fission products. Suitable nuclides are for example Sr-90/Y-90, Y-90 being the daughter nuclide of the fission product Sr-90, and Ce-144/Pr-144, Pr-144 being the daughter of the fission product Ce-144, and Ru-106/Rh-106, Rh-106 being the daughter of the fission product Ru-106.

The radioactive nuclide and/or precursor nuclide may be used in form of a material selected from the group consisting of elemental isotope mixtures enriched in the precursor nuclide higher than natural abundance, isotope mixtures depleted of isotopes giving rise to undesirable radiation emitting isotopes during the activation treatment, and mixtures thereof. The term "natural abundance" refers to an elemental isotope mixture with a natural isotopic composition, i.e. in case of palladium Pd-105, Pd-106 and Pd-108 dominate whereas Pd-102 is only present in a minor amount of about 1.0%.

In a preferred embodiment the radioactive nuclide is Pd-103 and/or its precursor Pd-102 and the metallic material (a) is Pd or an alloy thereof. In general palladium is selected from the group consisting of palladium enriched in Pd-102 higher than natural abundance, palladium depleted of isotopes giving rise to undesirable radiation emitting isotopes during the activation treatment, and mixtures thereof. In a preferred embodiment the Pd preferably comprises palladium enriched in Pd-102 higher than natural abundance. The term "natural abundance" refers to palladium with a natural isotopic composition, i.e. Pd-105, Pd-106 and Pd-108 dominate whereas Pd-102 is only present in a minor amount of about 1.0%. Any palladium comprising higher amounts of Pd-102 will be considered "enriched". Suitable for use will be any enriched Pd, preferably at least 5%, more preferably at least 20% and most preferably at least 50%. Typically enrichment is carried out up to 95%, more typically 50–90%. Of course any Pd can be used for practicing the present invention, as long as it comprises an activatable precursor of Pd-103 (e.g. Rh-103 or Pd-102), or Pd-103. Likewise suitable are e.g. Pd-isotope mixtures having a decreased content or depleted of isotopes (e.g. Pd-109, Pd-110) giving rise to undesirable radioactive isotopes such as Ag-110 m or Ag-111 upon activation.

Any elemental isotope mixture comprising higher than natural amounts of nuclide and/or precursor nuclide will be considered "enriched". Suitable for use will be any enriched mixture, the degree of enrichment depending on the radioactive nuclide/precursor nuclide chosen. Preferably enrichment is up to 100%. Likewise suitable are e.g elemental isotope mixtures having a decreased content or depleted of isotopes giving rise to undesirable radioactive isotopes upon activation; as described above for Pd.

The casing of the present invention may comprise up to 100% of the element of the desired nuclide in metallic form, e.g. may be of metallic Tm, or Pd. It may also consist of an alloy. In principle, each element being alloyable with the respective element/nuclide and optionally further alloying agents can be selected. The resulting alloy comprises at least two components, but may comprise further alloying components, provided the alloy can be processed to the closed and self-supported casing of the invention. The term "alloy" is defined broadly and encompasses homogeneous alloys, heterogeneous alloys as well as intermetallic compounds or carbonides, nitrides and carbonitrides of these metals and alloys. Corresponding alloying techniques are for example disclosed European patent application No. 99 118 544, which is incorporated by reference herein. In accordance with the present invention homogeneous alloys are preferred. Preferably, the casing consists of an alloy of the element with V, Ti, Al, Ni, Nb, Fe, stainless steel, and mixtures thereof. Vanadium and aluminum alloys are especially preferred since they enable manufacture of a casing with excellent mechanical properties.

All alloying materials and in general other metallic components of the seed (e.g. composite, coating, radio-opaque marker, sealing member) may be used in a form depleted of undesirable isotopes which during activation of the precursor nuclide give rise to undesirable radiation emitting isotopes. More preferably any alloying element or metal comprises a low capture cross-section and hence provides a minor shielding/self absorption effect both for activation radiation and/or more preferably the emitted radiation.

The casing of the present invention may also comprise a metal composite material of a metallic matrix, wherein the radioactive nuclide and/or precursor nuclide compound, selected e.g. from oxides, halides and mixtures, is embedded, preferably in [me divided form. The metal of the metallic matrix is selected from the above alloying materials, preferably Pd, Al, V, Ti, Ni, Nb, Fe, stainless steel, and mixtures thereof. The embedded compound is present in such an amount that the metallic processing properties of the matrix of the composite are preserved. Preferably, the compound is present in a minor amount of small particles (e.g. a powdered oxide) which are dispersed in the metal. According to the present invention the composite material may also have a lamellar structure with at least two alternating layers, wherein one layer type comprises the matrix and the other layer type comprises the nuclide and/or precursor nuclide compound or in metallic form.

Seeds according to the present invention are either radioactive or activatable. Radioactive seeds comprise the radioactive nuclide (e.g. Pd-103) whereas activatable seeds comprise the activatable precursor nuclide (e.g. Pd-102) thereof which precursor needs not be a radionuclide itself but can be converted to the same by using any suitable activation procedure. For example, Rh-103 represents a possible precursor being activated by exposure to a high-energy charged particle beam. The following tables 1 and 2 list suitable activatable precursor nuclides and the activation reaction for its conversion.

Further reference is made to the Karlsruher Nuklidkarte, 6$^{th}$ Ed., 1995, Forschungszentrum Karlsruhe, Germany.

TABLE 1

Table of suitable radioactive nuclides and precursor nuclides

| Element | Precursor Nuclide | Natural Abundance of Precursor (%) | Activation Reaction Type | Radio-active Nuclide | Cross section of Activation (barn) |
|---|---|---|---|---|---|
| Thulium | Tm-169 | 100 | (n,g) | Tm-170 | 105 |
| Yttrium | Y-89 | 100 | (n,g) | Y-90 | 1.25 |
| Ytterbium | Yb-168 | 0.13 | (n,g) | Yb-169 | 2400 |
| Phosphorous | P-31 | 100 | (n,g) | P-32 | 0.16 |
| Germanium | Ge-70 | 21 | (n,g) | Ge-71 | 3 |
| Selenium | Se-74 | 0.89 | (n,g) | Se-75 | 46 |
| Chlorine | Cl-35 | 76 | (n,g) | Cl-36 | 43.7 |
| Tantalum | Ta-181 | 99.99 | (n,g) | Ta-182 | 20 |
| Thallium | Tl-203 | 29.5 | (n,g) | Tl-204 | 11 |
| Tungsten | W-186 | 28.6 | (n,g) | W-188 | 36/70 via W-187 |
| Tin | Sn-122 | 4.63 | (n,g) | Sn-123 | 0.15 |
| Palladium | Rh-103 | 100 | (p,n), (d,2n) | Pd-103 | |
| Paladium | Pd-102 | 1.00 | (n,g) | Pd-103 | 3.2 |

(n,g) = neutron - gamma activation
(p,n) = proton bombardment
(d,dn) = deuteron

TABLE 2

Table of suitable radioactive fission product nuclides and decay nuclides

| Fission product | Mother Nuclide | Daughter nuclide |
|---|---|---|
| Sr-90 | Sr-90 | Y-90 |
| Ru-106 | Ru-106 | Rh-106 |
| | W-188 | Re-188 |
| Ce-144 | Ce-144 | Pr-144 |

Preferred activatable materials are materials activatable by the above nuclear reactions. More preferably these materials have a maximum particle energy of beta radiation of at least 500 keV and a photon energy for Y-radiation and/or x-ray radiation between 10 keV and 100 keV. These radioactive materials are soft emitters which are most desirably used in treatment of biologic materials due to their short attenuation distance, more in detail these materials are desirably due to their local ionizing effect and thus localized biological/material effect.

The activation process is a (n, g) reaction. For example, Palladium 102 is exposed in the neutron activation process to a neutron flux in a nuclear reactor to convert Pd-102 to Pd-103 by a (n, g) reaction (see e.g. WO 86/04248). The extent of conversion depends on the neutron flux intensity and the duration of the bombardment. In principle, the maximum of the Pd-102 to Pd-103 conversion ratio may be employed, but typically is not achieved or desirable, since higher conversions require highest flux irradiation. Partial conversion is thus typical and will provide a radioactive seed according to the present invention that can be used in radiotherapy. Preferably, only a minor amount of Pd-102 is converted to Pd-103.

Likewise, Tm-169 as the precursor nuclide, is exposed in the neutron activation process to a neutron flux in a nuclear reactor to convert the same to the desired radioactive nuclide, in the case of Tm-170 by a (n, g) reaction. The extent of conversion depends on the neutron flux intensity, enrichment, the respective capture cross-sections of the radioactive nuclide self and the precursor, and the duration of the bombardment. Again, in principle, maximum conversion ratios may be employed, but typically are not achieved or desirable, since higher conversions require highest flux irradiation. Partial conversion is thus typical and will provide a radioactive seed according to the present invention that can be used in radiotherapy. Preferably, only a minor amount of precursor nuclide is converted.

All of the radioactive nuclide is distributed within the metallic material forming the casing. According to the present invention, due to the metallic character of the material, alloy or composite used for the casing, no additional separate shell or casing is needed. The intensity of the emitted radiation such as X-rays or beta-particles is thus not attenuated since no additional absorber material (i.e. additional shell or casing) surrounds the emitting casing. Therefore the content of radioactive nuclide can be reduced to achieve the same therapeutic effect.

The apparent activity of the radioactive seed prepared from an activatable seed depends on the proportion of the activatable precursor being present in the casing as well as on the neutron beam intensity and the duration of the activation process. These parameters can be varied independently to generate an apparent activity which is therapeutically effective but does not damage healthy tissue. In general the chosen activity will depend on the intended final use of the seed and on the selected radioactive nuclide. In any case it can easily be determined by the skilled worker. Preferably, the activity of the radioactive seed is in the range from 0.1 $\mu$Ci up to 300 mCi, more preferably it is up to 50 mCi and even more preferred it is up to 5 mCi.

The seed of the invention may further comprise one or more coating(s). These coating(s) can be applied onto the casing by any coating technique known in the prior art, e.g. physical vapor deposition (PVD) including sputtering; chemical vapor deposition (CVD) including laser induced CVD, plasma activated CVD or thermal CVD; electrochemical coating; chemical coating like precipitation; thermal spraying processes like plasma spraying; deposition from metallic melt; dipping; immersion; plating etc.

In principle, any biocompatible material being coatable onto the casing can be used. The coating preferably strongly adheres to the outer casing surface and does not come off even in long term applications. Adhesion may be improved by surface treatments. Furthermore, the coating material preferably is corrosion resistant, resistant to radiation exposure (e.g. X-rays, neutrons, beta-particles etc.) during activation and emission and is not activated by the chosen activation treatment. The coating is further preferably physically robust e.g. has a suitable impact-resistance. To minimize any disadvantageous effects due to absorption the coating material has a low absorption coefficient with respect to the emitted radiation and a low neutron capture cross section in activation. The one or more coating(s) independently of each other preferably comprise a material selected from the group consisting of amorphous carbon, plastic materials, glass, amorphous silica, $SiO_2$, $Al_2O_3$, metals, metal alloys, nitrides, carbides, carbonitrides and mixtures thereof.

The coating process can be carried out such that any desirable coating thickness is generated. Preferably, the coating is as thin as possible to fulfill its barrier duties. In a preferred embodiment each coating has a thickness of 10 nm to 2 μm, preferably 20–100 nm, independent of the number of coatings (i.e. single coating or several coatings). The thickness may be used as an additional parameter to adjust the apparent activity of the seed due to X-ray absorption of the coating material. In a preferred embodiment the seed comprises only one coating.

More preferably, the seed comprises a first or only coating comprising amorphous carbon having a thickness of 10 nm to 2 μm, preferably 20–100 nm. Such a coating comprising amorphous carbon strongly adheres to the surface of the metallic casing of the invention, thus increasing mechanical stability and resistance to body fluids, especially in long-term applications. The term "amorphous" means that the deposited carbon does not have a regular crystal structure over an extended distance whereas the local structure in the range of neighboring atoms might be similar to crystalline modifications. Most preferably the coating of amorphous carbon is the only coating.

In a preferred embodiment the seed of the invention further comprises a radio-opaque marker which facilitates to determine and monitor its exact position inside the body. The radio-opaque marker includes any suitable material visible in X-ray or CTM applications. In particular, it includes one or more metals, alloys or metal compounds having a high atomic number (Z), preferably selected from the group consisting of Pb, Rh, Pt, Pd, Au, W, Ba, Ag, Cu, compounds comprising the same, and alloys e.g. with the above listed alloying elements and mixtures thereof. Preferably, Pb and/or Rh are used for cold assembly activation after complete assembly of the seed, whereas the other elements are preferably used in hot assembly of the seed.

The seed may further comprise means for fixing the radio-opaque marker inside the casing, preferably in a central position with respect to the surrounding casing. In case a rod shaped radio-opaque marker is used within the seed of the present invention, it preferably has a thickness of 0.1 to 0.8 mm, preferably 0.1 to 0.3 mm and a length corresponding to the length of the seed.

The seed of the present invention may further comprise a filler. The filler is in this case preferably selected from non-radioactive and non-activatable, low Z materials and may assist in fixing of the radio-opaque marker inside the casing. According to one embodiment the filler and the radio-opaque marker are used in form of a homogeneous particulate mixture, which is filled into the casing's central cavity the mixture comprising metallic or oxide particles/powders of marker and filler.

According to another embodiment the radio-opaque marker is a central rod, snuggly fitting into the hollow lumen of the tubular casing and the radio-opaque marker may be fixed, if necessary, by welding its ends to the endcaps of the tube and/or crushing/squeezing the ends of a longer coextruded rod of central marker surrounded by the casing material.

The casing of the invention may in general have any shape generating a closed and self-supported structure. Furthermore, the shape of the casing should be able to generate the desired homogeneous or patterned radiation field. Typically, for most applications a uniform and homogeneous radiation field around the seed is desired such that the surrounding tissue is exposed to a uniform radiation intensity. Preferred shapes are cylinders, doughnuts, spheres, oblongs.

The casing of the invention can comprise a body (2) having a central cavity or being a hollow structure such as a cylinder and may further comprise at least one, preferably one or two closure(s) or sealing member(s) (3). The body (2) preferably consists of the metallic material (a) as defined above optionally in combination with (b). The closure(s) or the sealing member(s) may consist of the metallic materials (a) and/or (b). In a preferred embodiment the body (2) is a hollow cylinder and the at least one closure consists of two endcaps.

BRIEF DESCRIPTION OF THE DRAWINGS

In the following the invention will be described in greater detail by reference to the illustrative embodiments shown in the figures. There are shown FIG. 1 shows a sectional drawing of a preferred embodiment of a closed and supported casing (1) comprising a tubular/cylindrical hemi-spherical part (2) provided with end caps (3) as the closures.

Figure 2:
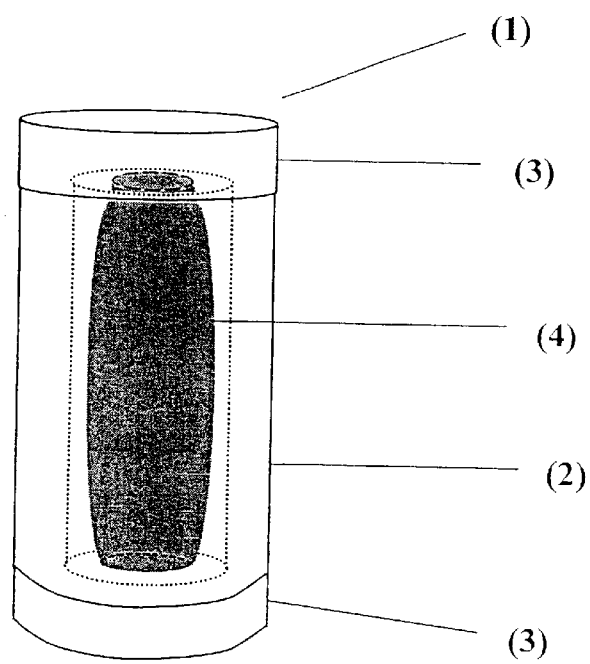
FIG. 2 shows a closed and self-supported casing (1) of the invention provided with a radio opaque marker (4)

FIG. 2 shows a closed and self-supported casing (1) having a tubular/cylindrical part (2) and flat disk-like end caps (3), additionally provided with a radio-opaque marker (4). As discussed below the radio opaque marker may be fixed by welding to the tubular part (2) and/or the end cap(s) (3).

Figure 3:
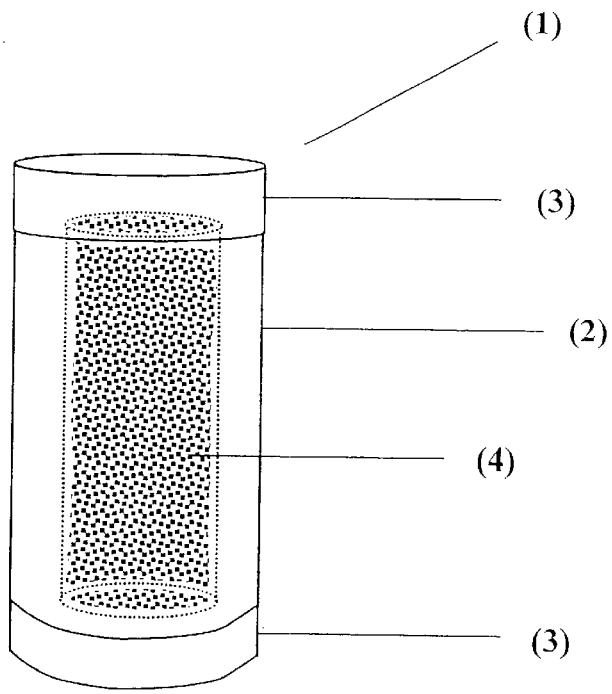
FIG. 3 shows a closed and self-supported casing (1) of the invention provided with a powder comprising a radio-opaque marker.

FIG. 3 shows a closed casing (1) having a tubular part (2) and end caps (3), which is provided with the filler and the radio-opaque marker in form of a homogeneous particulate mixture (4). The particulate mixture preferably takes up the entire closed volume of the casing.

DETAILED DESCRIPTION OF THE INVENTION

Preferably the casing in accordance with the present invention has closed cylindrical shape. Its dimensions are chosen such that for transportation to the predetermined position inside the body conventional equipment such as canules and needles can be used. Preferably, the casing has a length of 2.0 to 5.0 mm, more preferably 2.5 to 4.5 mm; an outer diameter of 0.3 to 2.0 mm, more preferably 0.4 to 0.8 mm; and a wall thickness of the casing of 10 to 250 μm, more preferably 30 to 100 μm. The exact dimensions and especially wall thickness of the seed may need adjustment by the skilled worker depending on the specific radioactive nuclide chosen, the desired emission etc. taking into account self absorption of the nuclide precursor. The wall thickness may also be used as a parameter to adjust the apparent activity of the seed since the amount of possibly radioactive material increases with increasing wall thickness. Furthermore, the wall thickness may be varied to ensure sufficient mechanical stability. Closure of the cylinder or generally any other hollow body may be achieved as discussed below by using end caps as the sealing members (3). These end caps may have various shapes. Preferably, they have the shape of a semi-sphere or a flat disk. Their diameter may be identical or very similar to the casing's diameter. Suitable designs of casings and end caps are e.g. disclosed in European patent application nos. 99 111 100.6 and 99 111 099.0 which are incorporated by reference.

In another preferred embodiment the body (2) of the casing comprises a hollow cylinder which is internally sealed by a second, optionally hollow cylinder as the sealing member (3), which is attached to the body at the edges thereof, although the sealing member may extend beyond the length of the body. The inner surface of the body and the outer surface of the sealing member define a closed volume between the first and second cylinder and thus a closed casing in accordance with the present invention. The joint or contact (7) between the body (2) and the sealing member (3) can be generated by any suitable technique, e.g. by welding, crimping or bonding. The second cylinder can be hollow, thereby providing a central opening, which e.g. allows for fixing the capsule on a suture, or may be solid. The second cylinder may comprise a metal of high atomic number (2) to form the radio-opaque marker. In this case the metal of the marker is preferably selected from the group consisting of Pb, Rh, Pt, Pd, Au, W, Ba, Ag, Cu, compounds comprising the same, and alloys and mixtures thereof. The second hollow cylinder (3) may completely consist of one of these metals or their mixtures. This embodiment is especially suitable for forming doughnut like seeds corresponding to or resembling short cylinders, internally sealed by the cylindrical sealing member, or for elongated tubes.

Figure 4:
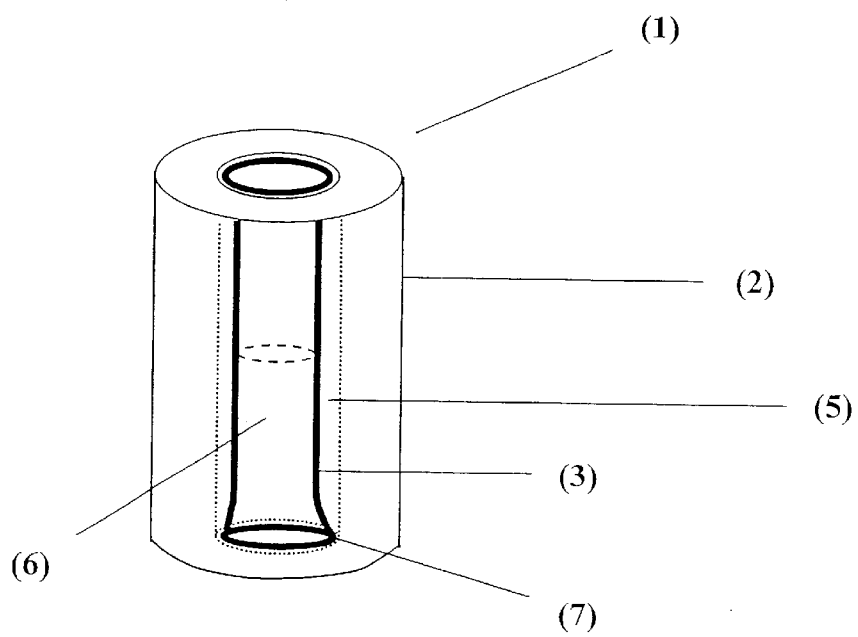
FIG. 4 shows a closed and self-supported casing (1) of the invention comprising a first hollow cylindrical tube (2) and a second hollow cylindrical tube (3).

In the above embodiment the body and sealing member generate a closed and self-supported casing having a passage through its three-dimensional structure. This passage enables to pass through a wire, suture or thread which helps to fix the seed at a predetermined position in the surrounding tissue. FIG. 4 shows such a casing (1) comprising a first hollow cylindrical tube (2) as the body and a second hollow cylindrical tube (3) as the sealing member, these tubes having contact areas (7) at their ends, thereby generating a closed volume (5) between both tubes and a passage (6) through the casing (1). The casing may, however, also be tightly fixed on the sealing member without forming an internal gap or lumen of the body.

The dimensions of the contact areas may vary. Preferably they are confined to the ends of both tubes. According to the present invention the length of body and the sealing member can be the same or different. Preferably, the length of the second tube (3) is, however, at least the length of the body (2). The wall thickness of the tubes can be the same or different.

According to another embodiment of the present invention, there is provided a method of preparation of a radioactive or activatable seed comprising the steps of a) providing the body of a closed and self-supported casing consisting of (a) a radioactive or activatable metallic material selected from the group consisting of a metal, an alloy and a metal composite or mixtures thereof, optionally in combination with (b) a non-radioactive, non-activatable metallic material; wherein (a) comprises a radioactive nuclide selected from the group consisting of Pd-103, Tm-170 Sr-90 Y-90 Yb-169 P-32 Ge-71 Se-75 Cl-36 Ta-182 Tl-204 Re-188, W-188, Ce-144, Pr-144, Sn-123, Ru-106, Rh-106 and mixtures thereof, and/or an activatable precursor nuclide thereof selected from the group consisting of Pd-102, Rh-103, Tm-169, Y-89, Yb-168, P-31, Ge-70, Se-74, Cl-35, Ta-181, Tl-203, W-186, Sn-122 and mixtures thereof, excluding metallic Pd with natural abundance of Pd-102;

b) optionally inserting a radio-opaque marker and/or a filler;

c) closing the casing; and d) optionally providing one or more coating(s).

In step a) the body of a closed casing is provided, i.e. manufacture of the casing is completed with the exception of closing the casing.

The closed and self-supported casing of the present invention can be manufactured using known and conventional metallurgical techniques. Any technique which enables to alloy, process and mould metallic materials of such small dimensions may be used. Suitable for casings in cylindrical form are e.g. extrusion of a tube, cutting the tube into the desired length and closing the tube by fixing endcaps thereon e.g. by welding, particularly laser welding, or by crimping. Another route of manufacture would comprise forming of an extruded hollow rod, crushing of a smaller length from the extruded rod, thereby closing the ends of the tube by squeezing them together, optionally followed by welding to round the ends. In case a radio-opaque marker is used, a core rod of the respective material can be co-extruded with the body and can be fIXed in its lumen by one of the above sealing methods (end cap or crushing).

When the hot assembly route (see above) is employed the casing provided in step a) may already comprise the radioactive nuclide without performing an activation process. Thus, additional safety measures will be necessary in the course of alloying the material or forming the composite and manufacturing the casing to avoid any radioactive contamination of equipment and personnel.

Preferably, the method for preparing a radioactive seed uses the cold assembly route which method may then further comprises a step of activating the precursor nuclide to yield the desired radioactive nuclide. In a preferred embodiment the precursor is Tm-169 or Pd-102 and activation occurs by neutron bombardment to yield Tm-170 and Pd-103, respectively.

The activation can be carried out in the presence of any neutron source generating neutron beams of sufficient intensity. Such neutron sources may be various types of nuclear fission reactors. The duration of the activation process depends on the desired apparent activity of the seed which is considered to be sufficient for generating a therapeutic effect. For suitable activation conditions and neutron fluxes see e.g. WO86/04248. For the purpose of the invention neutron fluxes of $1 \times 10^{13}$ to $3 \times 10^{15}$ $(cm^2 s)^{-1}$, preferably $1–20 \times 10^{14}$ $(cm^2 s)^{-1}$ at durations of 1 to 50 days, preferably 1 to 10 days for the cold assembly, are preferred. When the hot assembly route is used the optimum irradiation time before seed assembly, if necessary with the respective nuclide, is 1 to 12 weeks, preferably 2–8 weeks, and even more preferably 3–6 weeks and the optimum flux is $0.4–2 \times 10^{15}$ $(cm^2 s)^{-1}$. Of course the optimum fluxes and durations will depend on the nuclide chosen.

The radioactive nuclide may e.g. in case of Sr-90/Y-90 or Ce-144/Pr-144 likewise be obtained from nuclear fission as known in the art. In this case no cold assembly of the seed will be possible.

Typically only a fraction of the available precursor nuclide is converted. The final seed may thus comprise both the radioactive nuclide and its precursor (e.g. Tm-169 and Tm-170 or Pd-102 and Pd-103). Typically, the seed will comprise a large excess of the precursor as only a small fraction thereof is activated during activation treatment. In consequence the seed can be reactivated subsequent to a first therapeutic treatment by activating the remaining precursor nuclide.

According to the present invention activation may be carried out after different steps of the method of preparation. In a preferred embodiment activation is carried out after complete cold assembly of the seed in step d). Thus, subsequent to activation no further manufacturing steps with regard to seed assembly are necessary, thereby minimizing the risk of unnecessary radiation exposure of personnel and equipment. Furthermore, a production on demand of a radioactive seed is possible by activation of prefabricated seeds on demand, thereby avoiding any unnecessary decay of radioactive nuclide before therapeutic use. Considering the short half live of some of the nuclides used activation after complete cold assembly thus enables an effective therapeutic use of the seed according to the present invention.

In another preferred embodiment of the present invention activation is carried out after complete assembly of the seed in step c) before coating the seed, if used. This allows for use of e.g. polymeric coating materials which may not withstand activation conditions.

According to the present invention activation may also be carried out before inserting the radio-opaque marker and closing the casing. This will allow to use other materials than Pb and/or Rh for the marker as listed above which metals will otherwise either be activated themselves to yield undesirable contaminations or will not withstand activation conditions.

The invention will be further illustrated by reference to the following examples. The examples are given for illustration purposes only and are not intended to limit the scope of the invention.

EXAMPLE I

This example refers to an activation process using Pd with a degree of enrichment of 90% with respect to Pd-102. Table 1 gives the required amount of Pd and the corresponding volume percentage of Pd within the casing material to generate an apparent activity of 5 mCi at activation conditions.

In particular, seeds were manufactured by forming an alloy of Pd and V into a closed casing of cylindrical shape having a length of 4.5 mIn, an outer diameter of 0.8 $\mu$m and the wall thickness of which is i) 50 $\mu$m, ii) 40 $\mu$m or iii) 30 $\mu$m. The neutron flux used for activation is $2*10^{14}$ $(crn^2s)^{-1}$.

The following Table I shows the amount of Pd and the corresponding volume percentage of Pd with respect to the total volume of the casing material using different activation periods (i.e 1 day, 3 days or 10 days) to generate an apparent activity of 5 mCi.

TABLE I

Degree of enrichment = 90%

| | | Period of activation | | |
|---|---|---|---|---|
| | | 1 day | 3 days | 10 days |
| Volume percentage of Pd with regard to total volume of the casing Material | i) wall thickness 50 $\mu$m | 9.6% | 3.2% | 1.1% |
| | ii) wall thickness 40 $\mu$m | 12% | 4.0% | 1.4% |
| | iii) wall thickness 30 $\mu$m | 16% | 5.3% | 1.9% |

According to Table I only a minor amount of the casing material has to be Pd to generate an apparent activity of 5 mCi, provided the degree of enrichment with regard to Pd-102 is 90%. The amount of Pd can be further reduced using an extended period of activation or increasing the wall thickness of the casing. The remainder of the material i.e. for 30 $\mu$m thickness and 10 days activation 98.1% of the casing alloy was V, 94.7% V for 3 days and 84% for one day of activation.

EXAMPLE II

In Example II Example I was repeated, except that the degree of enrichment with regard to Pd-102 is 30%. The desired and measured apparent activity was 5 mCi, the neutron flux was $2*10^{14}$ $(cm^2s)^{-1}$. The casing had closed cylindrical shape having a length of 4.5 mm, an outer diameter of 0.8 mm and a wall thickness of i) 50 $\mu$m, ii) 40 $\mu$m or iii) 30 $\mu$m. As the alloying element V was used.

TABLE II

Degree of enrichment = 30%

| | | Period of activation | | |
|---|---|---|---|---|
| | | 1 day | 3 days | 10 days |
| | | total amount of Pd in the casing | | |
| | | 2.0 mg | 0.67 mg | 0.24 mg |
| volume percentage of Pd with regard to total volume of the casing material | i) wall thickness 50 $\mu$m | 28.7% | 9.6% | 3.4% |
| | ii) wall thickness 40 $\mu$m | 35.9% | 12% | 4.2% |
| | iii) wall thickness 30 $\mu$m | 47.9% | 16% | 5.6% |

As can be seen from this example a lower degree of enrichment allows for a smaller amount of allowing element (V) within the casing (for 30 $\mu$m 94.4% for 10 days, and only 52.1% for 1 day activation).

EXAMPLE III

In Example II Tm-169 of natural abundance was used as the precursor in form of an oxide. The indicated amounts of oxide was incorporated into metallic Al to form the metallic material (a) of the casing. The desired activity was 15 mCi. Activation occurred by neutron bombardment with a neutron flux of $4*10^{14}$ $(cm^2s)^{-1}$. The casing had closed cylindrical shape having a length of 2.5 mm, an outer diameter of 0.5 mm and a wall thickness of i) 50 $\mu$m, ii) 100 $\mu$m or iii) 150 $\mu$m.

TABLE II

Tm-casing (natural abundance)

| | | Period of Activation | | |
|---|---|---|---|---|
| | | 5 day | 10 days | 20 days |
| Mass percentage of Tm with regard to total mass of the casing material | i) wall thickness 50 $\mu$m | | 27% | 13% |
| | ii) wall thickness 100 $\mu$m | 29% | 14% | 7% |
| | iii) wall thickness 150 $\mu$m | 20% | 10% | 5% |

As can be seen from this example the mass percentage of Thuliumoxide in and $Tm_2O_3$/Al-composite of 5% is needed for a wall thickness of 150 $\mu$m in a 20 days activation period to achieve the desired activation of 15 mCi.

What is claimed is:

1. A radioactive or activatable seed comprising a closed and self-supported casing having a central cavity, the casing consisting of a radioactive or activatable metallic material selected from the group consisting of a metal, an alloy and metal composite or mixtures wherein the radioactive or activatable metallic material comprises a radioactive nuclide selected from the group consisting of Pd-103, Tm-170, Sr-90, Y-90, Yb-169, P-32, Ge-71, Se-75, Cl-36, Ta-182, Tl-204, Re-188, W-188, Ce-144, Pr-144, Sn-123, Ru-l06, Rh-106 and mixtures thereof, and/or an activatable precursor nuclide thereof selected from the group consisting of Pd-102, Rh-103, Tm-169, Y-89, Yb-168, P-31, Ge-70, Se-74, Cl-35, Ta-181, Tl-203, W-186, Sn-122 and mixtures thereof, excluding metallic Pd with natural abundance of Pd-102.

2. A seed according to claim 1, wherein the metal composite comprises a compound of the radioactive nuclide and/or activatable precursor nuclide selected from the group consisting of oxides, halides, phosphates and other salts and mixtures thereof; and wherein the composite further comprises a metal selected from the group consisting of Pd, Al, V, Ti, Ni, Nb, Fe, stainless steel and mixtures thereof.

3. A seed according to claim 1, further comprising one or more coatings.

4. A seed according to claim 1, further comprising a radio-opaque marker including a metal having a high atomic number (Z).

5. A seed according to claim 4, where in said metal is selected from the group consisting of Pb, Rh, Pt, Pd, Au, W, Ba, Ag, Cu, compounds comprising the same, and alloys and mixtures thereof.

6. A seed according to claim 1, wherein the radioactive nuclide is Pd-103 and/or the precursor nuclide is Pd-102.

7. A seed according to claim 1, wherein the radioactive nuclide is Tm-170 and/or the precursor nuclide is Tm-169.

8. A seed according to claim 1, wherein the casing (1) comprises a body (2) made from said metallic material, which body has a hollow structure, and at least one sealing member (2) made from the metallic material and/or non-radioactive and non-activatable metallic material.

9. A seed according to claim 1, wherein the body (2) is a hollow cylinder and wherein the sealing member (3) is either two endcaps or a second hollow cylinder disposed within the body which internally seal (s) the body (2).

10. A radioactive or activatable seed comprising: a closed and self-supported casing having a central cavity, the casing comprising: (a) a radioactive or activatable metallic material selected from the group consisting of a metal, an alloy and metal composite or mixtures thereof, and (b) optionally a non-radioactive and non-activatable metallic material; wherein the radioactive or activatable metallic material comprises a radioactive nuclide selected from the group consisting of Pd-103, Tm-170, Sr-90, Y-90, Yb-169, P-32, Ge-71, Se-75, Cl-36, Ta-182, Tl-204, Re-188, W-188, Ce-144, Pr-144, Sn-123, Ru-106, Rh-106 and mixtures thereof, and/or an activatable precursor nuclide thereof selected from the group consisting of Pd-102, Rh-103, Tm-169, Y-89, Yb-168, P-31, Ge-70, Se-74, Cl-35, Ta-181, Tl-203, W-186, Sn-122 and mixtures thereof, excluding metallic Pd with natural abundance of Pd-102, wherein the casing consists of an alloy of the radioactive nuclide and/or activatable precursor nuclide with V, Ti, Al, Ni, Nb, Fe, stainless steel and mixtures thereof.

11. A radioactive or activatable seed comprising: a closed and self-supported casing having a central cavity, the casing comprising: (a) a radioactive or activatable metallic material selected from the group consisting of a metal, an alloy and metal composite or mixtures thereof, and (b) optionally a non-radioactive and non-activatable metallic material; wherein the radioactive or activatable metallic material comprises a radioactive nuclide selected from the group consisting of Pd-103, Tm-170, Sr-90, Y-90, Yb-169, P-32, Ge-71, Se-75, Cl-36, Ta-182, Tl-204, Re-188, W-188, Ce-144, Pr-144, Sn-123, Ru-106, Rh-106 and mixtures thereof, and/or an activatable precursor nuclide thereof selected from the group consisting of Pd-102, Rh-103, Tm-169, Y-89, Yb-168, P-31, Ge-70, Se-74, Cl-35, Ta-181, Tl-203, W-186, Sn-122 and mixtures thereof, excluding metallic Pd with natural abundance of Pd-102, wherein the casing consists of an alloy of the radioactive nuclide and/or activatable precursor nuclide with V, Ti, Al, Ni, Nb, Fe, stainless steel and mixtures thereof, wherein the radioactive nuclide and/or activatable precursor nuclide is in the form of a material comprising the desired nuclide in natural abundance, a material enriched in the nuclide hi her than natural abundance or a material depleted of isotopes of the precursor element giving rise to undesirable radiation emitting isotopes during the activation treatment, and mixtures thereof.

12. A seed according to claim 11, wherein a material enriched in the activatable precursor nuclide is used and the degree of enrichment is at least 5% and up to 100%.

13. A seed according to claim 12, wherein the degree of enrichment is at least 20% and up to 100%.

14. A seed according to claim 12, wherein the degree of enrichment is from 50% to 90%.

15. A radioactive or activatable seed comprising: a closed and self-supported casing having a central cavity, the casing comprising: (a) a radioactive or activatable metallic material selected from the group consisting of a metal, an alloy and metal composite or mixtures thereof, (b) optionally a non-radioactive and non-activatable metallic material; wherein the radioactive or activatable metallic material comprises a radioactive nuclide selected from the group consisting of Pd-103, Tm-170, Sr-90, Y-90, Yb-169, P-32, Ge-71, Se-75, Cl-36, Ta-182, Tl-204, Re-188, W-188, Ce-144, Pr-144, Sn-123, Ru-106, Rh-106 and mixtures thereof, and/or an activatable precursor nuclide thereof selected from the group consisting of Pd-102, Rh-103, Tm-169, Y-89, Yb-168, P-31, Ge-70, Se-74, Cl-35, Ta-181, Tl-203, W-186, Sn-122 and mixtures thereof, excluding metallic Pd with natural abundance of Pd-102, and (c) a first coating comprising amorphous carbon and having a thickness of 10 nm to 2 $\mu$m.

16. The seed according to claim 15, wherein the first coating comprising amorphous carbon has a thickness of 20 nm to 100 nm.

17. A method of preparation of a radioactive or activatable seed, the method comprising the steps of:
  a) providing a body of a closed and self-supported casing having a central cavity, wherein the casing consists of a radioactive or activatable metallic material selected from the group consisting of a metal, an alloy and a metal composite or mixtures thereof;
  wherein the radioactive or activatable metallic material comprises a radioactive nuclide selected from the group consisting of Pd-103, Tm-170, Sr-90, Y-90, Yb-169, P-32, Ge-71, Se-75, Cl-36, Ta-182, Tl-204, Re-188, W-188, Ce-144, Pr-144, Sn-123, Ru-106, Rh-106 and mixtures thereof, and/or an activatable precursor nuclide thereof selected from the group consisting of Pd-102, Rh-103, Tm-169, Y-89, Yb-168, P-31, Ge-70, Se-74, Cl-35, Ta-181, Tl-203, W-186, Sn-122 and mixtures thereof, excluding metallic Pd with natural abundance of Pd-102;
  b) optionally inserting a radio-opaque marker and/or a filler;
  c) closing the casing; and
  d) optionally providing one or more coating(s).

18. A method according to claim 17, wherein the casing is closed by welding or crimping.

19. A method according to claim 17 for preparing a radioactive seed, further comprising a step of activating the precursor nuclide selected from the group consisting of Pd-102, Rh-103, Tm-169, Y-89, Yb-168, P-31, Ge-70, Se-74, Cl-35, Ta-181, Tl-203, W-186, Sn-122 and mixtures thereof by neutron bombardment or charged particles bombardment in the case of Rh-103.

20. The method according to claim 19, wherein activation is carried out after complete assembly of the seed in step c) or in step d).

21. The method according to claim 19, wherein activation is carried out before inserting the radio-opaque marker and closing the casing.

* * * * *

UNITED STATES PATENT AND TRADEMARK OFFICE
CERTIFICATE OF CORRECTION

PATENT NO. : 6,716,156 B2
DATED : April 6, 2004
INVENTOR(S) : Helmut Menuhr, Eberhard Fritz and Mark Shilton It is certified that error appears in the above-identified patent and that said Letters Patent is hereby corrected as shown below:

<u>Title page,</u>
Item [73], Assignee, should read as -- Assignee: AEA Technology QSA GmbH (DE) --

<u>Column 2,</u>
Line 39, "EP-A-I, OO8,995" should read as -- EP-A-1,008,995 --

Signed and Sealed this

Twenty-fifth Day of May, 2004

JON W. DUDAS
*Acting Director of the United States Patent and Trademark Office*